United States Patent [19]
Häusler et al.

[11] Patent Number: 6,150,145
[45] Date of Patent: Nov. 21, 2000

[54] PROCESS FOR THE PRODUCTION OF DEGRADATION PRODUCTS OF FATTY ACIDS

[75] Inventors: Alex Häusler, Madeira, Ohio; Charles Ehret, Wetzikon; Eva Binggeli, Pfaffhausen, both of Switzerland

[73] Assignee: Givaudan Roure (International) SA, Vernier, Switzerland

[21] Appl. No.: 09/177,354

[22] Filed: Oct. 23, 1998

[30] Foreign Application Priority Data

Oct. 23, 1997 [EP] European Pat. Off. .............. 97810790

[51] Int. Cl.⁷ ....................................................... C12P 7/24
[52] U.S. Cl. .......................... 435/147; 435/155; 568/449; 568/910
[58] Field of Search ..................... 435/123, 125, 435/126, 147, 148, 155, 171; 568/449, 910

[56] References Cited

U.S. PATENT DOCUMENTS

| | | | |
|---|---|---|---|
| 4,668,433 | 5/1987 | Ochsner | 252/522 R |
| 5,464,761 | 11/1995 | Muller et al. | 435/147 |
| 5,705,372 | 1/1998 | Belin et al. | 435/123 |

FOREIGN PATENT DOCUMENTS

| | | | |
|---|---|---|---|
| 2 696 192 A1 | 9/1992 | France . | |
| WO 93/24644 | 12/1993 | WIPO . | |
| WO 94/08028 | 4/1994 | WIPO . | |
| WO 95/26413 | 10/1995 | WIPO . | |

OTHER PUBLICATIONS

Chemical Abstracts, vol. 126, No. 12, Abstract No. 157337 (1997).
Chemical Abstracts, vol. 125, No. 24, Abstract No. 308625 (1996).
Chemical Abstracts, vol. 122, No. 25, Abstract No. 313385 (1995).
Chemical Abstracts, vol. 122, No. 25, Abstract No. 313167 (1995).
Chemical Abstracts, vol. 91, No. 23, Abstract No. 189842 (1979).
Chemical Abstracts, vol. 68, No. 9, Abstract No. 38321 (1968).
Chemical Abstracts, vol. 84, No. 21, Abstract No. 147748 (1976).

*Primary Examiner*—Sreeni Padmanabhan
*Attorney, Agent, or Firm*—Mark E. Waddell; Stephen M. Haracz; Bryan Cave LLP

[57] ABSTRACT

Fatty acid degradation products are over-produced by oxidative biochemical degradation of a plant biomass containing unsaturated fatty acids and enzymes for the degradation in the presence of additional unsaturated fatty acids. These degradation products are natural flavour and fragrance ingredients.

16 Claims, No Drawings

PROCESS FOR THE PRODUCTION OF DEGRADATION PRODUCTS OF FATTY ACIDS

BACKGROUND OF THE INVENTION

The present invention relates to a process for the production of degradation products of unsaturated fatty acids. These degradation products are volatile natural flavour and fragrance ingredients. These ingredients include but are not restricted to trans-2-cis-6-nonadienal, trans-2 cis-6-nonadien-1-ol, green note compounds such as cis-3-hexen-1-ol, trans-2-hexenal and improved complex flavour and fragrance mixtures such as natural plant extracts and absolutes. The above ingredients are present in a wide variety of fruits, leaves, vegetables and other plant constituents. Due to their pronounced impact on flavour and fragrance of these plants, they are widely used as impact ingredients in flavour and fragrance compositions. Their organoleptic characteristics range from fresh, grassy, "green", to cucumber- and melonlike.

Natural short chain, $C_6$-aldehydes and $C_6$-alcohols, the so-called "green note" compounds are currently isolated from plants or their essential oils (e.g. mint oil). They can also be biosynthetically produced. The FR-A1 2696 192 describes the production of ionones and aldehydes by contacting a natural source of polyunsaturated fatty acids with lipoxgenases, hydroxyperoxide lyases and a natural source of carotene in a liquid medium. The WO 95/26413 discloses the conversion of linolenic acid to cis-3-hexen-1-ol in presence of lipoxygenase, hydroperoxyde lyase and yeast. The degradation of polyunsaturated fatty acids according the state of the art is induced by the oxygenation reaction at cis-cis double bonds of these fatty acids. The oxygenation is catalyzed by lipoxygenase (EC 1.13.11.12)-enzymes. The oxygenated products, fatty acid hydroperoxides, are the precursors for many important hormones (e.g. prostaglandins) and of flavour and fragrance molecules. In plants, cleavage of the hydroperoxides occurs through the action of specific hydroperoxide lyases.

Natural $C_9$-aldehydes and $C_9$-alcohols (e.g trans-2-cis-6-nonadienal, trans-2-cis-6-nonadien-1-ol) as such are not available on the market and, so far, can only be used in flavour and fragrance compositions via the violet (Viola odorata L.) leaf absolute. The important constituents present in violet leaf extracts among others are: trans-2-cis-6-nonadienal, trans-2-cis-6-nonadien-1-ol, 1-octen-3-ol, cis-3-hexenyl alcohol and cis-3-hexenyl-acetate. All these compounds are derived from the oxidative degradation of fatty acids present in the violet leaves. The violet leaf absolute has a typical green fatty note similar to that of cucumbers and is predominantly used as fragrance component, but also as natural flavour ingredient in e.g. tropical fruit flavours for its fruity-cucumber character. Violet leaf absolute is therefore widely used in a great variety of flavour and fragrance compositions.

Due to the solubility characteristics of the absolute and the presence of other natural by-notes such as the flowery ionones and the fatty acids, it cannot be used in all requested dosages for flavour applications. It is therefore highly desirable to provide the above natural $C_9$-aldehydes and $C_9$-alcohols in a higher concentration with a relatively lower content of other by-notes.

SUMMARY OF THE INVENTION

The present invention provides a process for the production of fatty acid degradation products, especially $C_9$-aldehydes and $C_9$-alcohols, by oxidative biochemical degradation of unsaturated fatty acids. The process is characterized by oxidative biochemical degradation of a plant biomass containing fatty acids and enzymes for the oxidative degradation in the presence of additional unsaturated fatty acids.

DETAILED DESCRIPTION OF THE INVENTION

The specific enzymes present in the various plant materials catalyze the degradation of fatty acids to important flavour and fragrance products. The present process takes advantage of the presence of these enzymes to degrade also the additional fatty acids and thereby overproducing the desired compounds. In particular, according to the process of the invention natural $C_9$-aldehydes and $C_9$-alcohols are overproduced in the presence of additional precursor fatty acids. In addition to the overproduction of the desired compounds less undesired by-products are obtained and the solubility characteristics of the extract or absolute is improved. The invention provides improved complex flavour and fragrance mixtures such as natural plant extracts and absolutes. Examples of desired degradation products are trans-2-cis-6-nonadienal, trans-2-cis-6-nonadien-1-ol and green note compounds such as cis-3-hexen-1-ol and trans-2-hexenal.

Plant material used for the process of the invention containing the precursor fatty acids as well is enzymes for degrading the precursor fatty acids are well known to the skilled person. The precursor fatty acids and enzymes are present in a wide variety of fruits, leaves, vegetables and other plant constituents. Therefore, a variety of plant material can be used to carry out the process of the invention. Preferred are plants which are rich in the necessary enzymes for the specific degradation of the fatty acids (e.g. lipoxygenase and hydroperoxide lyase). The product obtained using such plant material depends on the specificity of the enzymes present in these plants. For six-carbon aliphatic aldehydes and alcohols, plants containing high levels of lipoxygenase with a C-13 specificity are preferred. For nine-carbon aliphatic aldehydes and alcohols, plants with lipoxygenase with a C-9 specificity are preferred. It is also possible to combine material from more than one specific plant in order to obtain an optimized distribution of the desired enzymes.

Representative plant materials include: violet (Viola odorata L.) leaves; cucumber (Cucumis sativus) leaves, seeds and fruits; melon (Cucumis melo) leaves, seeds and fruits; watermelon (Citrullus lanatus) leaves, seeds and fruits; pumpkin (Cucurbita maxima) leaves, seeds and fruits; pear (Pirus piraster) leaves and fruits; borage (Borago officinalis) leaves; tomato (Lycopersicon lycopersicum) leaves and fruits; potato (Solanum tuberosum) leaves and tuber; and soybean (Glycine max) fruit and seed. It is a matter of course, that it is not possible to give a complete list of plant materials which can be used as enzyme sources.

The precursor unsaturated fatty acids are added to the plant material at once or at different stages of the process. They may be added to the disintegrated plant material, the biomass or to the plant material before or after harvesting. The precursor unsaturated fatty acids include among others: linoleic acid, (alpha- and gamma-) linolenic acid, arachidonic acid, eicosapentaenoic acid and docosahexaenoic acid. Different unsaturated fatty acids may be applied before and after harvesting.

The preferred plant material is violet leaf. Violet leaves are available almost all year round and are cultured mainly in the southern part of France (i.e. region of Grasse). These leaves are harvested at least three times per year. Therefore, plant material on a large scale is available. Plants grown in a greenhouse are also useful for the process of the invention.

The plant material has to be harvested without inactivating the endogeneous enzymes, i.e. the plant leaves have to be kept intact. Preferably the plant material is stored for as short a period as possible and under controlled humidity conditions, in order not to inactivate the enzymes present in the plant material by drying. If a longer period of storage is necessary, the plant material should be kept under cool conditions (4° to 10° C.) for not more than about ten days.

Unexpectedly, prior spraying of the harvested plant material with an unsaturated fatty acid in addition to a precursor fatty acid added to the actual biochemical reaction led to increased yields of the process. It is therefore preferred to spray the plant material with a mixture of precursor fatty acid (e.g. linolenic acid) in water or a buffer solution between 1 and 24 hrs, preferably between 5 and 16 hrs, prior to the actual biochemical degradation reaction. Alternatively or additionally, the precursor fatty acid composition may be sprayed before harvesting onto the plant material. The plant material can be treated repeatedly in intervals of days or only once, prior to processing it to a biomass.

The unsaturated fatty acids to be added to the plant material can be prepared by known methods such as treatment of vegetable oils with a commercial lipase. The amount of unsaturated fatty acid used in the current process depends on various factors such as levels of enzyme activity present in the plant material, desired product etc. Typically, unsaturated fatty acids are used in amounts of about 0.1% to 10%, preferably 1% to 5%, of the weight of the plant material.

A number of fatty acid degradation products useful as natural flavour and fragrance ingredients can be provided by the process of the present invention. Examples for flavour and fragrance ingredients prepared by the process of the invention are: trans-2-cis-6-nonadienal, trans-2-cis-6 nonadien-1-ol, cis-3-hexen-1-ol, trans-2-hexenal, cis-3-hexenal, cis-3-cis-6-nonadienal, cis-3-cis6-nonadien-1-ol, hexanal, hexanol, cis-3-nonenal, cis-3-nonen-1-ol, trans-2-nonenal, trans-2 nonen-1-ol, trans-2-cis-6-nonadienyl ethylester and mixtures thereof, contained in violet leaf absolute and other plant extracts and absolutes. The preferred ingredients include trans-2-cis-6-nonadienal and a violet leaf absolute with an increased content of natural trans-2-cis-6-nonadienal and trans-2-cis-6-nonadien-1-ol.

To convert aliphatic aldehydes obtained by the process of the invention into alcohols, alcohol dehydrogenase may be added. As a source of alcohol dehydrogenase, active baker's yeast cells may be used.

For the biochemical reaction, the plant material is mixed with the fatty acid or its solution and with water or a buffer solution successively or simultaneously. The ratio of aqueous liquid to plant material can vary in the range from 1 to 1 up to 10 to 1, preferably 5 to 1 on a weight basis. Immediately after mixing, the plant material is sheared and blended to obtain a biomass. As a buffer solution, typically a 10 to 100 mM solution of sodium or potassium phosphate buffer is used. A supply of air has to be guaranteed during the reaction.

It is important that the plant material is disintegrated very finely in order to increase the release of active enzymes. The precursor unsaturated fatty acid can be added simultaneously with the disintegration or on a continuous basis as the biochemical reaction proceeds very fast. The disintegration is usually continued for 10 to 60 min. Typically the reaction mixture is maintained during the degradation reaction at room temperature (i.e. between 15 to 25° C.). The plant material is disintegrated by techniques such as high speed blenders, mixers, shearing or chopping devices.

The desired compounds can be isolated from the reaction slurry by standard methods such as steam distillation. The distillate can be extracted with a suitable solvent such as hexane or methyl-t-butylether. After separation of aqueous and organic phases, the product is obtained from the organic phase by evaporation of the solvent. Alternatively, the reaction slurry may be extracted with a suitable solvent such as hexane or methyl-t-butylether. After evaporation of the solvent, the resulting product is dissolved in ethanol and the ethanol insoluble material is precipitated by cooling the solution to −10° C. for 10 to 24 hrs. The ethanol insoluble material is subsequently removed by centrifugation and the ethanol is evaporated to yield a new quality of violet leaf absolute.

The process of the invention provides an overproduction of the degradation products. The treatment of plant material with the additional unsaturated fatty acid prior to the actual biochemical reaction to which the precursor fatty acid is added enhances the yields of the desired product further significantly. The process provides a new and efficient method for the over-production of natural aliphatic aldehydes and alcohols, preferably $C_9$-aldehydes and $C_9$-alcohols, in mixtures e.g. extracts of reaction slurries which may be further purified. The process yields, depending on the quality of the plant material and the conditions of the process, more than 100 mg and under preferred conditions more than 600 mg per kg plant material of trans-2-cis-6-nonadienal and more than 10 mg per kg plant material of trans-2-cis-6-nonadien-1-ol. The process also provides in excess of 25 g per kg plant material of violet leaf absolute with a content of trans-2-cis-6-nonadienal and trans-2-cis-6-nonadien-1-ol in excess of 0.4%.

EXAMPLE 1

SMALL SCALE PRODUCTION OF TRANS-2-CIS-6-NONADIENAL

Preparation of Linseed Oil Lipolysate 50 ml of phosphate buffer (pH 7.3; 0.2 M), 50 ml linseed oil (Roth AG, Karlsruhe, Germany) and 50 mg lipase "Candida cylindracea" (Biocatalysts Ltd., Pontypridd, UK) were mixed in a shaking flask. The mixture was shaken for 24 hrs at 37° C. at 220 rpm and subsequently centrifuged. The upper phase (linseed oil lipolysate) was collected.

Generation of $C_9$-aldehydes and $C_9$-alcohols

Using a small nebulizer, 300 g of harvested violet leaves were sprayed with a mixture of: 100 ml sodium phosphate buffer (50 mM, pH 6.5), 2 ml of linseed oil lipolysate and 120 $\mu$l of Antifoam Dow 1520. The moistened leaves were left at room temperature for 17 hrs. Then 20 g of the spray-treated violet leaves, 100 ml of sodium phosphate buffer (50 mM, pH 6.5) and 1 ml of linseed oil lipolysate were added to a Waring blender. The mixture was sheared for 2 min. at high speed setting and was subsequently transferred to a three-necked flask equipped with a mechanical stirrer. The reaction mixture was stirred at 700 rpm for 30 min. at room temperature during which time air was continuously added to the headspace. For determination of the content of $C_9$-aldehydes and -alcohols, 10 ml of the reaction mixture was steam distilled and the resulting water phase was subsequently extracted with 2 ml methyl-t-butylether. The amount of individual volatiles was determined by gas chromatographic analysis. The amounts of trans-2-cis-6-nonadienal and trans-2-cis-6-nonadienol were 661 mg and 44 mg respectively, per kg plant material processed. Among others the following additional compounds were found in the reaction mixture: hexanal, cis-3-hexenal, cis-3-hexenol, trans-2-hexenal, trans-2-hexenol, 1-octen-3-ol, trans-2-nonenal.

EXAMPLE 2

PILOT-SCALE PRODUCTION OF TRANS-2-CIS-6-NONADIENAL

Preparation of Linseed Oil Lipolysate 1500 ml of phosphate buffer (pH 7.3; 0.2 M), 1500 ml linseed oil and 1500 mg lipase "Candida cylindracea" were mixed in a stirring vessel. The mixture was stirred for 24 hrs at 37° C. and 220 rpm and subsequently centrifuged. The upper phase (linseed oil lipolysate) was collected.

Production of Trans-2-cis-6-nonadienal

The following ingredients were mixed in a spray pump: 0.4 kg of sodium phosphate buffer (1 M, pH 6.5), 7.6 kg of tap water, 0.167 kg of linseed oil lipolysate, 10 g of Antifoam Dow 1520. 24 kg of harvested violet leaves were sprayed with the above mixture using the spray pump. Mixing was periodically repeated to avoid separation of the phases (water/fatty acid). The leaves were turned and spraying was repeated once. Then the moistened leaves were left for 17 hrs at room temperature.

Six reaction batches were performed. For each batch 19 kg of tap water, 1 kg of sodium phosphate buffer (1 M, pH 6.5) and 0.2 kg of linseed oil lipolysate were filled into a 30 l mixer-cutter (Stephan UM44; A. Stephan u. Söhne GmbH & Co., Hameln, Germany) equipped with rotating knives. The ingredients were mixed shortly to form an emulsion. 4 kg of pretreated leaves were added to the emulsion and cut for 30 min. while air was introduced.

The six reaction batches were pooled and 50 kg of tap water was added to the mixture. The volatiles were isolated by steam-distillation. A total of 62 l of distillate was collected which was subsequently extracted with 5 l of hexane. The solvent was evaporated on a rotavapor at 50° C. and 20 mbar vacuum. Residual water was removed manually using a separatory funnel. After removal of the solvent 7.9 g of product was obtained with a content of 75% of trans-2-cis-6-nonadienal.

EXAMPLE 3

Production of Trans-2-cis-6-nonadienal

The linseed oil lipolysate was prepared as described in Example 2.

Before harvesting, violet plants were sprayed using a spray pump with the following mixture: 0.4 kg of sodium phosphate buffer (1 M, pH 6.5), 7.6 kg of tap water, 0.167 kg of linseed oil lipolysate, 10 g of Antifoam Dow 1520. The plant material was harvested 17 hrs after spraying and used directly for the production of $C_9$-aldehydes and $C_9$-alcohols. 19 kg of tap water, 1 kg of sodium phosphate buffer (1 M, pH 6.5) and 0.2 kg of linseed oil lipolysate were filled into a 30 l mixer-cutter (Stephan UM44) equipped with rotating knives. The ingredients were mixed shortly to form an emulsion. 4 kg of pretreated freshly harvested leaves were added to the emulsion and cut for 30 min. while air was introduced.

The volatiles were isolated by steam-distillation. The distillate was collected and subsequently extracted with 0.8 l of hexane. The solvent was evaporated on a vacuum rotavapor at 50° C. and 20 mbar vacuum. Residual water was removed manually using a separatory funnel. The $C_9$-aldehydes and $C_9$-alcohols were identified by gas chromatography.

EXAMPLE 4

Production of a Violet Leaf Absolute

Production of linseed oil lipolysate and of the reaction mixture was as described in Example 2. 0.5 l of the reaction mixture was extracted with an equal volume of hexane. The plant particulate material was removed by filtration through three layers of cheesecloth ("Miracloth", Calbiochem-Novabiochem Corp., La Jolla, Calif., USA). The filtrate was transferred into a separatory funnel and the aqueous phase was removed. The organic phase was washed three times with 250 ml of 1 M NaCl. Subsequently, the solvent was evaporated on a rotavapor at 50° C. and 80 mbar vacuum. The thus obtained "concrete" was dissolved in 8 volumes parts of cold ethanol per 1 weight part of concrete and stirred in a three necked flask for 20 hrs at −10° C.

The precipitate formed was removed from the ethanolic solution by centrifugation (5000×g, 15 min.) and the solvent was evaporated on a rotavapor (50° C., 80 mbar vacuum). 2.7 g of absolute was obtained with a content of 0.4% trans-2-cis-6-nonadienal, corresponding to approximately 28 g absolute per kg of violet leaves.

While the invention has been described with respect to illustrative embodiments and modes of practice, it will be apparent to those skilled in the art that various modifications and improvements may be made without departing from the scope of the present invention.

What is claimed is:

1. A process for the production of fatty acid degradation products by oxidative biochemical degradation of unsaturated fatty acids characterized by oxidative biochemical degradation of a plant biomass containing unsaturated fatty acids and enzymes for the oxidative degradation in the presence of an additional unsaturated fatty acid which is sprayed onto the plant material prior to the biochemical reaction and for the biochemical reaction the plant material is mixed with the fatty acid and water and the plant material is disintegrated to the plant biomass.

2. The process according to claim 1, further comprising adding the additional unsaturated fatty acid to the plant biomass composition which comprises a harvested plant material.

3. The process according to claim 1, further comprising adding the additional unsaturated fatty acid to the plant material during the oxidative degradation.

4. The process according to claim 1, further comprising spraying the plant material at least once with the additional unsaturated fatty acid up to 24 hours prior to the oxidative degradation.

5. The process according to claim 4, wherein the spraying is from 5 to 16 hours prior to the oxidative degradation.

6. The process according to claim 1, further comprising adding the additional unsaturated acids to the plant material before it is harvested.

7. The process according to claim 1, wherein the additional unsaturated fatty acid is linolenic acid.

8. The process according to claim 1, wherein the fatty acid degradation products comprise aliphatic $C_9$-aldehydes and $C_9$-alcohols.

9. The process according to claim 1, wherein the enzymes comprise lipoxygenase.

10. The process according to claim 1, wherein the enzymes comprise hydroperoxid lyase.

11. The process according to claim 1, wherein the plant material of the plant biomass composition is disintegrated violet leaves.

12. The process according to claim 1, further comprising disintegrating plant material in a buffer solution to obtain a starting biomass.

13. Flavor and fragrance compositions obtained according to the process of claim 1.

14. A process for the production of fatty acid degradation products, comprising the steps of:
   a) providing a plant material comprising unsaturated fatty acids and enzymes required for oxidative biochemical degradation of unsaturated fatty acids;
   b) applying an additional unsaturated fatty acid to the plant material prior to initiation of the oxidative biochemical degradation reaction that forms the fatty acid degradation products;
   c) mixing the plant material and the additional unsaturated fatty acid; and
   d) disintegrating the plant material in the presence of the additional unsaturated fatty acid and a supply of air.

15. The process according to claim 14, wherein the unsaturated fatty acids are added to the plant material prior to and during the disintegrating of the plant material.

16. Flavor and fragrance composition obtained according to the process of claim 14.

* * * * *